United States Patent
Salas et al.

(10) Patent No.: US 9,518,297 B2
(45) Date of Patent: Dec. 13, 2016

(54) THROMBOEMBOLIC DISEASE MARKERS

(75) Inventors: Eduardo Salas, Barcelona (ES); José Manuel Soria, Barcelona (ES); Miroslava Ogorelkova, Barcelona (ES); Roberto Elosua Llanos, Barcelona (ES); Joan Vila, Barcelona (ES); Sergio Castillo, Barcelona (ES)

(73) Assignee: Gendiag.exe, S.L., Barcelona (ES)

( * ) Notice: Subject to any disclaimer, the term of this patent is extended or adjusted under 35 U.S.C. 154(b) by 170 days.

(21) Appl. No.: 14/126,624

(22) PCT Filed: Jun. 13, 2012

(86) PCT No.: PCT/EP2012/061185
§ 371 (c)(1),
(2), (4) Date: Mar. 4, 2014

(87) PCT Pub. No.: WO2012/171949
PCT Pub. Date: Dec. 20, 2012

(65) Prior Publication Data
US 2014/0221230 A1    Aug. 7, 2014

(30) Foreign Application Priority Data
Jun. 16, 2011    (EP) ................... 11170235

(51) Int. Cl.
*C12Q 1/68* (2006.01)
*C07H 21/04* (2006.01)

(52) U.S. Cl.
CPC .......... *C12Q 1/6883* (2013.01); *C12Q 1/6827* (2013.01); *C12Q 1/6837* (2013.01); *C12Q 2600/106* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2003/0092019 A1* | 5/2003 | Meyer | C07K 14/47 435/6.14 |
| 2005/0026168 A1 | 2/2005 | Xie | |
| 2007/0054275 A1 | 3/2007 | Dogulu et al. | |
| 2007/0160992 A1 | 7/2007 | Bortolin et al. | |

FOREIGN PATENT DOCUMENTS

| | | |
|---|---|---|
| EP | 1 398 388 A2 | 3/2004 |
| EP | 1 684 202 A1 | 7/2006 |
| WO | WO 02/14555 A2 | 2/2002 |
| WO | WO 2004/083225 A2 | 9/2004 |
| WO | WO 2008/020090 A1 | 2/2008 |

OTHER PUBLICATIONS

DeHann et al. (Blood, vol. 120, No. 3, pp. 656-662, Jul. 2012).*
Soria et al. (Rev Esp Cardiol, Supp. 2009, vol. 9, pp. 58B-65B).*
Flinterman et al. (BJH, vol. 149, pp. 118-123, Jan. 20, 2010).*
Debette et al. Circulation, vol. 2, No. 2, pp. 191-198, Apr. 2009).*
Pennisi, Science, 1998; 281 (5384):1787-1789.*
Lucentini The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Buchholz et al., Inherited thrombophilia: impact on human reproduction. Am J Reprod Immunol. Jul. 2003;50(1):20-32.
Corral et al., A nonsense polymorphism in the protein Z-dependent protease inhibitor increases the risk for venous thrombosis. Blood. Jul. 1, 2006;108(1):177-83. Epub Mar. 9, 2006.
Corral et al., Antithrombin Cambridge II (A384S): an underestimated genetic risk factor for venous thrombosis. Blood. May 15, 2007;109(10):4258-63. Epub Jan. 23, 2007.
Debette et al., Genetics of atherothrombotic and lacunar stroke. Circ Cardiovasc Genet. Apr. 2009;2(2):191-8. doi: 10.1161/CIRCGENETICS.108.828319. Online Supplemental Material.
Delluc et al., Association of common genetic variations and idiopathic venous thromboembolism. Results from EDITh, a hospital-based case-control study. Thromb Haemost. Jun. 2010;103(6):1161-9. doi: 10.1160/TH09-07-0430. Epub Mar. 29, 2010.
Erali et al., Evaluation of electronic microarrays for genotyping factor V, factor II, and MTHFR. Clin Chem. May 2003;49(5):732-9.
Franco et al., Genetic Variations of the Hemostatic System as Risk Factors for Venous and Arterial Thrombotic Disease. Current Genomics. May 2003;4(4):309-336.
Glueck et al., Estrogen replacement therapy, thrombophilia, and atherothrombosis. Metabolism. Jun. 2002;51(6):724-32.
Harper et al., The incidence of dysfunctional antithrombin variants: four cases in 210 patients with thromboembolic disease. Br J Haematol. Mar. 1991;77(3):360-4.
Heit et al., Genetic variation within the anticoagulant, procoagulant, fibrinolytic and innate immunity pathways as risk factors for venous thromboembolism. J Thromb Haemost. Jun. 2011;9(6):1133-42. doi: 10.1111/j.1538-7836.2011.04272.x.
Johnson et al., The factor XII–4C>T variant and risk of common thrombotic disorders: A HuGE review and meta-analysis of evidence from observational studies. Am J Epidemiol. Jan. 15, 2011;173(2):136-44. doi: 10.1093/aje/kwq349. Epub Nov. 11, 2010.
Lowe, Common risk factors for both arterial and venous thrombosis. Br J Haematol. Mar. 2008;140(5):488-95. doi: 10.1111/j.1365-2141.2007.06973.x.
Mannila et al., Epistatic and pleiotropic effects of polymorphisms in the fibrinogen and coagulation factor XIII genes on plasma fibrinogen concentration, fibrin gel structure and risk of myocardial infarction. Thromb Haemost. Mar. 2006;95(3):420-7.

(Continued)

*Primary Examiner* — Jeanine A Goldberg
(74) *Attorney, Agent, or Firm* — Wolf, Greenfield & Sacks, P.C.

(57) ABSTRACT

The invention relates to a method for a more appropriate thromboembolic event risk assessment based on the presence of different genetic variant. The invention also relates to a method for determining the risk of suffering a thromboembolism disease by combining the absence or presence of one or more polymorphic markers in a sample from the subject with conventional risk factors for thromboembolism as well as computer-implemented means for carrying out said method.

5 Claims, 1 Drawing Sheet

(56) References Cited

OTHER PUBLICATIONS

Morelli et al., ABO blood group genotypes and the risk of venous thrombosis: effect of factor V Leiden. J Thromb Haemost. Jan. 2005;3(1):183-5.

Olsson et al., Polymorphism and recombination events at the ABO locus: a major challenge for genomic ABO blood grouping strategies. Transfus Med. Aug. 2001;11(4):295-313.

Ray et al., Genetics University of Toronto Thrombophilia Study in Women (GUTTSI): genetic and.other risk factors for venous thromboembolism in women. Curr Control Trials Cardiovasc Med 2001;2(3):141-149.

Reid et al., DNA-based methods in the immunohematology reference laboratory. Transfus Apher Sci. Feb. 2011;44(1):65-72. doi: 10.1016/j.transci.2010.12.011. Epub Jan. 22, 2011.

Satra et al., Sequence variations in the FII, FV, F13A1, FGB and PAI-1 genes are associated with differences in myocardial perfusion. Pharmacogenomics. Feb. 2011;12(2):195-203. doi:10.2217/pp. 10.180. Erratum in: Pharmacogenomics. Apr. 2011;12(4):596. Wosniak, Greta [corrected to Wozniak, Greta].

Szolnoki et al., Evaluation of the modifying effects of unfavourable genotypes on classical clinical risk factors for ischaemic stroke. J Neurol Neurosurg Psychiatry. Dec. 2003;74(12):1615-20.

Van Der Neut Kolfschoten et al., The activated protein C (APC)-resistant phenotype of APC cleavage site mutants of recombinant factor V in a reconstituted plasma model. Blood Coagul Fibrinolysis. Apr. 2002;13(3):207-15.

Wiggins et al., ABO genotype and risk of thrombotic events and hemorrhagic stroke. J Thromb Haemost. Feb. 2009;7(2):263-9. doi: 10.1111/j.1538-7836.2008.03243.x. Epub Nov. 25, 2008.

Ye et al., Seven haemostatic gene polymorphisms in coronary disease: meta-analysis of 66,155 cases and 91,307 controls. Lancet. Feb. 25, 2006;367(9511):651-8.

Yip, Sequence variation at the human ABO locus. Ann Hum Genet. Jan. 2002;66(Pt 1):1-27.

Patent Examination Report No. 1 for Australian application No. 2012269112 issued Apr. 13, 2015.

Cote et al., Tobacco and estrogen metabolic polymorphisms and risk of non-small cell lung cancer in women. Carcinogenesis. Apr. 2009;30(4):626-35. doi: 10.1093/carcin/bgp033. Epub Jan. 27, 2009.

Hosmer et al., Parametric Regression Models. Chapter 8. In: Applied Survival Analysis: Regression Modeling of Time to Event Data. 2008. 244-285.

EP 1416550.7, Mar. 9, 2015, Extended European Search Report.

\* cited by examiner

THROMBOEMBOLIC DISEASE MARKERS

RELATED APPLICATION

This application is a national stage filing under 35 U.S.C. §371 of international application PCT/EP2012/061185, filed Jun. 13, 2012, which was published under PCT Article 21(2) in English, the disclosure of which is incorporated by reference herein in its entirety.

FIELD OF THE INVENTION

The present invention relates to the field of thromboembolic diseases or disorders. More specifically, it relates to markers and methods for determining whether a subject, particularly a human subject, is at risk of developing thromboembolic disease or disorder, developing a thromboembolic event, having thromboembolic disease or disorder, or experiencing a complication of a thromboembolic disease.

TECHNICAL BACKGROUND

Thromboembolic disease is the leading cause of morbidity and mortality in the developed world (America Heart Association 2010. Circulation 2010;121:e46-e215). Arterial thrombosis is the most common underlying cause of acute myocardial infarction, non-hemorrhagic cerebrovascular accidents, and peripheral vascular disease. Pathological manifestations of venous thromboembolism (VTE) largely include deep vein thrombosis (DVT) and pulmonary embolus (PE). While arterial thromboembolic events are the foremost cause of death and disability, venous disease also plays an important role. VTE occurs for the first time in 100 per 100 000 persons each year in the United States (America Heart Association 2010. Circulation 2010;121:e46-e215). Approximately one third of patients with symptomatic VTE manifest PE, whereas two thirds manifest DVT alone (America Heart Association 2010. Circulation 2010;121: e46-e215). PE is the most common cause of preventable hospital death accounting for 60.000 deaths in the United States annually (Anderson F A. Arch Intem Med 1991:151: 933-8, Spencer F A. Arch Inter Med 168:425-430).

Medical textbooks and epidemiological studies characteristically consider arterial and venous thromboembolic disease as distinct entities, each with their own pathophysiological basis, unique risk factors, and distinct therapeutic regimens (Bauer K A. Hematology Am Soc Hematol Educ Program 2002;353-368). Arterial clots typically occur in an injured vessel and the most common cause of vascular damage in the arterial system is atherosclerotic vascular disease (AVD) (Lane D E 2000. Thromb Haemost 2000;76: 651-62). The risk factors for arterial thrombosis are therefore considered the same as those for AVD. Arterial clots occur in a high flow, high shear environment and these clots, also called white clots, are rich in platelets. Prevention and treatment of arterial thrombosis is often aimed at platelet inhibition. While vascular injury can promote the formation of venous clots, stasis and changes in blood composition (thrombophilia) are the most important risk factors for venous clot development (Lane D E 2000. Thromb Haemost 2000;76:651-62). Venous clots occur in a low flow system, they are rich in fibrin that is enmeshed with red blood cells and are referred to as red clots. Inhibition of fibrin formation is the mainstay of prevention and treatment of venous thrombosis. It is often reported that the risk factors for arterial and venous thrombosis largely differ (Bauer K A. Hematology Am Soc Hematol Educ Program 2002;353-368).

However, recent studies have demonstrated a close association between arterial and venous thrombosis at a variety of levels. Specifically it has been shown that:
1) arterial and venous thrombosis share common risk factors (Doggen C J M Arteroscler Thromb Vasc Biol 2004;24: 1970-5, Goldhaber S Z In: Bloom A L, Forbes C D, Thomas D P, Tuddenham E G D, eds. Hemostasis and Thrombosis. New York: Churchill and Livingstone: 1997; 1327-1333),
2) individuals who suffer idiopathic venous thromboembolism are at a markedly increased risk of suffering a significant cardiovascular event (Becattini C. European Heart Journal 2005;26:77-83),
3) individuals who suffer idiopathic venous thromboembolism have an increased incidence of atherosclerotic vascular disease (Becattini C. European Heart Journal 2005; 26:77-83),
and
4) those who suffer idiopathic venous thromboembolism have a significantly higher incidence of metabolic syndrome (Ageno W. J Thromb Haemost 2006;4:1914-8).

The risk factors reported to be common to both arterial and venous thrombosis and that represent significant hazard for the development of each entity include increasing age and weight, smoking, exposure to estrogens, and the presence of diabetes. It has also been shown that high HDL cholesterol levels are associated with a decreased risk of venous thrombosis while elevated triglyceride and/or total cholesterol levels convey an increased risk. Other risk factors reported to be common to both arterial and venous thrombosis include the presence of antiphospholipid antibodies, dysfibrinogenemia, hyperhomocysteinemia, and elevated levels of fibrinogen, lipoprotein (a) and factor VIII.

One of the strongest pieces of evidence in favour of a link between arterial and venous thrombosis is the Genetic Analysis of Idiopathic Thrombophilia (GAIT) Study (Souto J C. Am J Hum Genet 2000:67:1452-1459). This family-based study of the genetics of thrombosis in a Spanish population was initiated to determine the heritability of thrombosis. Three hundred and twenty-eight individuals in 21 extended pedigrees were evaluated using a novel computer assisted adaptation of a multivariate threshold model. The authors concluded that more than 60% of the variation in susceptibility to common thrombosis is attributable to genetic factors. What makes this study unusual is that both venous and arterial thromboembolic events were included in the analysis. When venous and arterial thrombosis were jointly analyzed, arterial and venous thromboses were highly genetically correlated. That is, many of the same genes are involved in the pathogenesis of arterial and venous disease.

There are also studies (Doggen C J M, Smith N L, Lamahre R N, et al. Arteros Thromb Vasc Biol 2004;24: 1970-5; Becattini E. European Heart Journal 2005;26:77-83; Ageno W.] Thromb Haemost 4:1914-8) suggesting that arterial and venous thrombosis represent different manifestations of the same disease and that the underlying process is driven by a common set of genes.

A) Prevention of First Episode of Thromboembolism

Symptomatic thrombosis (arterial o venous) is a multi-factorial disease that manifests when a person with an underlying predisposition to thrombosis (thrombophilia also referred to as thrombophilic disorder or hypercoagulable syndromes) is exposed to clinical risk factors.

Assessment of presence of thrombophilia is not solely confined to laboratory testing but begins with a detailed history and physical examination. Detailed inquiry into symptoms and signs of acquired risk factors (coexisting diseases, medication exposure, and clinical circumstances) that are associated with thrombosis are an important part of the initial evaluation as is a complete physical examination. In addition to judicious laboratory testing appropriate for the patient's age and symptoms, objective confirmation of venous thromboembolism is critical.

Laboratory Testing

Currently, there is no single laboratory global assay that will 'screen' for the presence of thrombophilia. Thus, laboratory testing can be broadly categorized into (1) general diagnostic testing, (2) specialized coagulation testing, and (3) ancillary testing for disorders known to predispose to thrombotic disorders.

Specialized Coagulation Testing

Special Coagulation testing consists of a battery of complex (protein and DNA-based) thrombophilia assays to detect presence of an inherited or acquired thrombophilia. However, multiple preanalytical conditions affect results of the non-DNA-based assays (e.g. anticoagulants, acute thrombosis, liver disease, etc), so interpretation of results needs to be done within the context of the circumstances surrounding testing. An additional factor affecting the yield of testing is the ethnicity of the patient population being studied. Prevalence of factor V Leiden (FVL) varies from 3% to 7% in Caucasians of European ancestry, but has a very low prevalence in individuals of other ethnic groups: 0% among Native Americans/Australians and Africans, 0.16% among the Chinese, and 0.6% among individuals from Asia Minor (India, Pakistan, Sri Lanka). The ethnicity is important especially when few (one or two) genetic markers are analysed.

Factors Affecting Results of Protein-Based Specialized Coagulation Testing.

Effect of Acute Thrombosis

During the acute thrombotic episode, levels of antithrombin, protein C, and protein S may be transiently reduced; thus, if testing is not repeated, remote from the thrombotic event and from anticoagulant therapy, the patient may be misdiagnosed as having a congenital deficiency.

Effect of Anticoagulants

Heparin. Heparin therapy can falsely reduce antithrombin levels. Although most lupus anticoagulant (LAC) reagents [e.g. dilute russel viper venom time (DRVVT) and Stadot APTT] contain heparin neutralizers that can neutralize up to 1 U/mL of heparin, presence of excess heparin may result in a false-positive test result, which impacts the duration of secondary prophylaxis. Thus, positive results of LAC testing performed while on heparin should be reconfirmed when the patient is off heparin.

Vitamin K antagonist (VKA) therapy. Protein C and S levels are lowered by VKA therapy (e.g. warfarin since they are vitamin K-dependent proteins). In addition, VKA therapy may result in a false-positive LAC with certain assays (e.g. DRVVT).

Direct thrombin inhibitors (DTIs; e.g. argatroban, lepirudin, bivalirudin). Because the majority of anticoagulant activity assays rely on generation of thrombin to achieve an endpoint of dot detection, presence of DTIs interfere with this endpoint and delay dot formation. This can lead to a false-positive LAC or falsely reduced protein C and S levels. Results of chromogenic assays are likely reliable.

Effect of Liver Disease

The majority of anticoagulant and procoagulant proteins are produced in the liver. In advanced liver disease, levels of both the anticoagulant and procoagulant proteins are reduced.

Sample Collection and Processing Issues

Practically speaking, ordering physicians have limited impact on specimen collection and processing; however, knowledge of such effects may lead one to consider repeat testing, if the data are unexpected or do not fit the expected pattern [e.g. reduced activated protein C resistance (APC-R) ratio suggesting presence of APC-R, yet the FVL test is negative].

Effect of Type of Anticoagulant in Specimen Collection Tube

Standard specimen collection tubes contain 0.105-0.109 mol citrate for optimal results. Specimens may inadvertently be collected in ethylenediaminetetraacetic acid (EDTA), which will result in falsely reduced protein levels and a reduced APC-R ratio.

Effect of Specimen Processing

Specimens should be double centrifuged as soon as possible after collection in order to reduce the amount of residual platelets to a minimum. The presence of residual platelets can result in a false-negative test for LAC.

Molecular Risk for Thrombotic Disease

Although an inherited tendency for excessive bleeding is often be ascribed to single or few gene abnormalities, there is ample evidence to suggest that, in contrast, the clinical manifestations of hypercoagulability are usually the result of adverse interactions between multiple genes and the environment. Thus, the use of molecular diagnostics to document markers of thrombotic risk (thrombophilia) will prove to be far more challenging than with the inherited hemorrhagic disorders. To further complicate matters, despite the fact that with appropriate testing, thrombophilic mutations can be identified in patients following a first clinical episode of venous thromboembolism, interpretation of these results remains problematic.

Inherited Resistance to Activated Protein C: Factor V Leiden

Until 1994, the investigation of patients with clinical evidence of hypercoagulability was usually unproductive. However, with the discovery by Dahlback and Hildebrand of an inherited form of resistance to the proteolytic effects of activated protein C, and the subsequent finding of a common missense mutation in the factor V gene by Bertina and colleagues in Leiden, a major advance was made in the laboratory assessment of thrombotic risk.

The Leiden mutation substitutes a glutamine for an arginine at amino acid residue 506 in factor V, the initial cleavage site for activated protein C. The mutation is readily detected by a number of PCR-based approaches. Between 2% and 5% of individuals in Western populations have been documented to be heterozygous for factor V Leiden. In contrast, the mutation is extremely rare in subjects of Asian and African descent.

In some laboratories, initial screening for resistance to activated protein C is performed using the prolongation of an activated partial thromboplastin time-based assay as an indicator; patients testing positive (prolongation in the presence of factor V-deficient plasma) are subsequently evaluated by a PCR.

Increasingly, where access to PCR-based molecular analysis is routine, laboratories will more often choose to proceed directly to the genetic test, as the result is definitive and more than 95% of activated protein C resistance is a result of this single mutation.

Persons heterozygous for the factor V Leiden mutation have an approximately five-fold increased relative risk of venous thrombosis. It is found in 15-20% of patients experiencing their first episode of venous thrombosis. The hypercoagulable phenotype associated with factor V Leiden shows incomplete penetrance, and some individuals may never manifest a clinical thrombotic event. In contrast to the increased relative risk for an initial venous thrombotic event associated with factor V Leiden, this genetic variant is not associated with increased risks for either arterial thrombosis or a recurrence of venous thrombosis. Coinheritance of other inherited thrombotic risk factors or exposure to environmental risk factors can dramatically enhance the thrombotic risk in carriers of factor V Leiden. Many clinicians test for this disorder in patients with a family history of thrombosis who are about to be exposed to an acquired thrombotic risk factor. Individuals homozygous for the mutation have a 70-fold enhanced relative risk of venous thrombosis, indicating that this phenotype is transmitted as a codominant trait.

Prothrombin 20210 3' Non-Coding Sequence Variant

In 1996, Poort and colleagues described an association between a G to A nucleotide polymorphism at position 20210 in the 3' untranslated region (UTR) of the prothrombin gene, increased plasma levels of prothrombin, and an enhanced risk for venous thrombosis. This polymorphic nucleotide substitution is at the very end of the 3' UTR and exerts its effect on prothrombin levels in the heterozygous state. Although the plasma levels of prothrombin in subjects heterozygous for this polymorphism are higher on average than those in individuals with a normal prothrombin genotype, levels are usually still within the normal range. As a consequence, this polymorphism can only be evaluated by genetic testing, which is achieved by a PCR-based assay, most often now involving a form of real-time quantitative assay.

As with the factor V Leiden genotype, the prevalence of the prothrombin 20210 G to A variant in the general population is relatively high at 1-5%. This variant is also rare in persons of Asian and African descent. The heterozygous state is associated with a two-to four-fold increase in the relative risk for venous thrombosis. There is no influence on venous thrombotic recurrence. The relationship of prothrombin G2010A with arterial thrombosis is very modest (OR 1.32; 95% CI 1.03-1.69) (Kim R J. Am Heart J 2003;146:948-957).

Thermolabile C671T 5,10-Methylene-Tetrahydrofolate Reductase Variant

The third, high-prevalence gene tic variant that was initially thought to be associated with an increased thrombotic risk is the C to T variant at nucleotide 677 (an alanine to valine substitution) in the 5,10-methylene-tetrahydrofolate reductase (MTHFR) gene. This genotype results in expression of an enzyme with increased thermolability. Homozygosity for the variant is associated with hyperhomocysteinemia, particularly in the presence of folate deficiency. In many populations (southern Europeans and Hispanic Americans), approximately 10% of subjects are homozygous for the C677T variant, a sequence change that can easily be detected by a PCR-based strategy. However, after further extended analysis, in contrast to the factor V Leiden and prothrombin 20210 variants, the role of the MTHFR C677T polymorphism as an independent risk factor for venous thromboembolism appears minor.

B) Diagnosis of Venous Thromboembolism

Objective testing for deep vein thrombosis and pulmonary embolism is essential because clinical assessment alone is unreliable. Failure to diagnose venous thromboembolism is associated with a high mortality, whereas inappropriate anticoagulation can lead to serious complications, including fatal haemorrhage.

Diagnosis of Deep Vein Thrombosis

The clinical features of deep vein thrombosis include localized swelling, erythema, tenderness, and distal edema. However, these features are nonspecific, and approximately 85% of ambulatory patients with suspected deep vein thrombosis will have another cause for their symptoms. The differential diagnosis for deep vein thrombosis includes:
   cellulites;
   ruptured Baker cyst;
   muscle tear, muscle cramps, muscle hematoma;
   external venous compression;
   superficial thrombophlebitis; and
   post-thrombotic syndrome.

Venography

Venography is the reference standard test for the diagnosis of deep vein thrombosis. It has advantages over other tests in that it is capable of detecting both proximal vein thrombosis and isolated calf vein thrombosis. However, the disadvantages are that it:
   is invasive, expensive, and requires technical expertise; and
   exposes patients to the risks associated with contrast media, including the potential for an allergic reaction or renal impairment.

For these reasons, noninvasive tests such as venous ultrasonography and D-dimer testing, alone or in combination with clinical assessment, have largely replaced venography.

Compression Venous Ultrasonography

This is the noninvasive method of choice for diagnosing DVT. The common femoral vein, superficial femoral vein, popliteal vein, and proximal deep calf veins are imaged in real time and compressed with the transducer probe. Inability 10 compress the vein fully is diagnostic of venous thrombosis. Venous ultrasonography is highly accurate for the detection of proximal vein thrombosis with a sensitivity of approximately 97%, specificity of approximately 94%, and negative predictive value of approximately 98% in symptomatic patients. If DVT cannot be excluded by a normal proximal venous ultrasound in combination with other results (e.g. low clinical probability or normal D-dimer), a follow-up ultrasound is performed after 1 week to check for extending calf vein thrombosis (present in approximately 2% of patients). If the second ultrasound is normal, the risk of symptomatic VTE during the next 6 months is less than 2%.

The accuracy of venous ultrasonography is substantially lower if its findings are discordant with the clinical assessment and/or if abnormalities are confined to short segments of the deep veins. Ideally, these patients should have a venogram because the result of the venogram will differ from the venous ultrasound in approximately 25% of these cases. If venography is not available, additional testing (e.g. D-dimer, serial venous ultrasonography) may help to clarify the diagnosis and avoid inappropriate anticoagulant therapy.

Venous ultrasonography of the calf veins is more difficult to perform (e.g. sensitivity 70%), and its value is controversial. Some investigators have proposed that a single complete compression ultrasound that includes examination of the calf veins should be used to exclude DVT. Studies using this method have reported an incidence of VTE of 0.5% during 3 months follow-up after a negative examination, establishing that a negative venous ultrasound that includes the calf veins excludes VTE [8]. However, this method has the potential to diagnose calf DVT that would have spontaneously lysed without treatment and to yield false-positive results, thereby exposing patients to the risk of bleeding due to anticoagulant therapy without clear benefit.

D-Dimer Blood Testing

D-dimer is formed when cross-linked fibrin is broken down by plasmin, and levels are usually elevated with DVT and/or PE. Normal levels can help to exclude VTE, but elevated D-dimer levels are non-specific and have low positive predictive value. D-dimer assays differ markedly in their diagnostic properties for VTE. A normal result with a very sensitive D-dimer assay (i.e. sensitivity of approximately 98%) excludes VTE on its own [i.e. it has a high negative predictive value (NPV). However, very sensitive D-dimer tests have low specificity (approximately 40%), which limits their use because of high false positive rates. In order to exclude DVT and/or PE, a normal result with a less sensitive D-dimer assay (i.e. approximately 85%) needs to be combined with either a low clinical probability or another objective test that has a high NPV, but is non-diagnostic on its own (e.g., negative venous ultrasound of the proximal veins. As less sensitive D-dimer assays are more specific (approximately 70%), they yield fewer false-positive results.

Specificity of D-dimer decreases with aging and with comorbid/illness, such as cancer. Consequently, D-dimer testing may have limited value as a diagnostic test for VTE in hospitalized patients (more false positive results) and is unhelpful in the early postoperative period.

Computed Tomographic (CT) Venography and Magnetic Resonance (MR) Venography

CT venography and MR venography have the potential to diagnose DVT in settings where the accuracy of compression ultrasonography is limited (e.g. isolated pelvic DVT, asymptomatic patients). The sensitivity and specificity of CT venography compared with compression ultrasonography for detecting all DVT has been reported between 89% and 100%, and 94% and 100%, respectively. However, given the cost, exposure to radiation, and limited availability of CT venography, this modality currently plays a limited role in the diagnosis of DVT. A meta-analysis of studies comparing MR venography with conventional venography reported a pooled sensitivity of 92% and specificity of 95% of MR venography for proximal DVT. As with CT venography, cost and availability will inhibit the widespread use of MR for diagnosis of acute DVT.

Diagnosis of Pulmonary embolism (PE)

The clinical features of PE may include:
pleuritic chest pain,
shortness of breath.
syncope.
hemoptysis, and
palpitations.

As with DVT, these features are non-specific, and objective testing must be performed to confirm or exclude the diagnosis of PE.

Pulmonary Angiography

This is the reference standard test for the diagnosis of PE. However, it has many of the same limitations as venography.

Computed Tomographic Pulmonary Angiography (CTPA)

Spiral CT (also know as helical CT) with peripheral injection of radiographic contrast (CTPA) is the current standard diagnostic test for PE (Stein P D. N Engl J Med 2006;354:2317-2327, Roy P M. Br Med J 2005;331:259). In comparison with ventilation-perfusion lung scanning, CTPA is less likely to be "non-diagnostic" (i.e. approximately 10% vs. 60%) and has the potential to identify an alternative etiology for the patient's symptoms. This technique has a sensitivity of 83%, specificity of 96%, NPV of 95%, and positive predictive value of 86% for PE.

Accuracy of CTP A varies according to the size of the largest pulmonary artery involved and according to clinical pretest probability. For example, the positive predictive value of CTPA is 97% for pulmonary emboli in the main or lobar artery, but drops to 68% for segmental arteries, and is lower still for PE in the subsegmental arteries (25%). In patients with a high clinical pretest probability of PE, the positive predictive value of CTPA is 96%, but this value falls to 92% in patients with a technical pretest probability of PE, and to 58% in patients with a low clinical pretest probability of PE.

In management studies that used CTP A to diagnose PE, less than 2% of patients who had anticoagulant therapy withheld based on a negative CTPA went on to have symptomatic VTE during follow-up. Taken together, these observations suggest the following:

A good-quality, normal CTPA excludes PE if clinical suspicion is low or moderate.

Lobar or larger pulmonary artery intraluminal defects are generally diagnostic for PE.

Segmental pulmonary artery intraluminal defects are generally diagnostic for PE if clinical suspicion is moderate or high, but should be considered non-diagnostic if suspicion is low or there are discordant findings (e.g. negative D-dimer).

Subsegmental pulmonary artery intraluminal defects are nondiagnostic, and patients with such findings require further testing.

A note of caution: If possible, CTPA should be avoided in younger women (e.g. younger than 40 years) because it delivers a substantial dose of radiation to the chest, which increases the risk of breast cancer.

Ventilation-Perfusion Lung Scanning

In the past, ventilation-perfusion lung scanning was the initial investigation in patients with suspected PE, and it is still useful in patients with contraindications to x-ray contrast dye (e.g. renal failure) and patients at higher risk for developing breast cancer from radiation exposure (e.g. young women). A normal perfusion scan excludes PE, but is only found in a minority of patients (10-40%). Perfusion defects are non-specific; only approximately one-third of patients with perfusion defects have PE. The probability that a perfusion defect is caused by PE increases with size and number and the presence of a normal ventilation scan ("mismatched" defect). A lung scan with mismatched segmental or larger perfusion defects is termed "high-probability." A single mismatched defect is associated with a prevalence of PE of approximately 80%. Three or more mismatched defects are associated with a prevalence of PE of approximately 90%. Lung scan findings are highly age-dependent, with a relatively high proportion of normal scans and a low proportion of non-diagnostic scans in younger patients. A high frequency of normal lung scans is also seen in pregnant patients who are investigated for PE.

Clinical Assessment:

As with suspected DVT, clinical assessment is useful for categorizing probability of PE.

D-Dimer Testing:

As previously discussed when considering the diagnosis of DVT, a normal D-dimer result, alone or in combination with another negative test, can be used to exclude PE.

Patients with Nondiagnostic Combinations of Noninvasive Tests for PE

Patients with non-diagnostic test results for PE at presentation have a prevalence of PE of approximately 20%; therefore, further investigations to exclude PE are required.

Diagnosis of PE in Pregnancy

Pregnant patients with suspected PE can be managed similarly to non-pregnant patients, with the following modifications:

- Venous ultrasound of the legs should be performed first followed by ventilation-perfusion lung scanning if there is no DVT.
- The amount of radioisotope used for the perfusion scan should be reduced and the duration of scanning extended.
- If pulmonary angiography is performed, the brachial approach with abdominal screening is preferred.
- The use of CTPA in pregnancy is discouraged, primarily because of radiation exposure to the mother.

C) Risk of Recurrence after a First Episode of Symptomatic Venous Thromboembolism Venous thromboembolism is associated with diverse risk factors, some of which are transient, such as recent surgery and pregnancy, and others of which are persistent, such as cancer (Table 1 shows the risk factors for venous thromboembolism). When venous thromboembolism is associated with an acquired risk factor, either transient or persistent, it is called provoked. When there is no apparent clinical risk factor, it is called unprovoked or idiopathic.

TABLE 1

| Risk factors for venous thromboembolism |
|---|
| Major transient risk factors |
| Hospitalization |
| Plaster cast immobilization |
| Surgery |
| Trauma |
| Minor transient risk factors |
| Oral contraceptives or hormone therapy |
| Pregnancy |
| Presence of major risk factors 1 to 3 months before venous thromboembolism |
| Prolonged travel (≥2 hours) |
| Potential acquired or persistent risk factors |
| Collagen vascular diseases |
| Heart failure |
| Malignancy |
| Medications |
| Myelo proliferative disorders |
| Nephrotic syndrome |

It has recently been recognized that the presence or absence of a transient, or reversible, risk factor at the time of venous thromboembolism strongly affects the risk of recurrence after anticoagulant therapy is stopped. Patients with venous thromboembolism provoked by a transient risk factor have a low risk of recurrence compared with patients with either venous thromboembolism provoked by a persistent risk factor or unprovoked venous thromboembolism (Alfonso Iorio. Arch Intern Med 2010;170:1710-1716). For this reason, patients with venous thromboembolism provoked by a transient risk factor are usually treated with anticoagulant agents for 3 months (Alfonso Iorio. Arch Intern Med 2010;170:1710-1716), whereas patients with venous thromboembolism that was not associated with a transient risk factor are often treated long-term (Alfonso Iorio. Arch Intern Med 2010;170:1710-1716). The cumulative risk of recurrence at one, five, and 10 years is 15, 41, and 53 percent, respectively, in patients with an idiopathic venous thromboembolism, compared with 7, 16, and 23 percent in patients with a provoked event (Galioto N J. Am Fam Physician 2011;83:293-300).

Although it is widely accepted that the risk of recurrence in patients with venous thromboembolism provoked by a transient risk factor is low enough to justify stopping anticoagulant therapy after 3 months, this recurrence risk is not well quantified. Furthermore, the risk of recurrence may not be the same in all patients with venous thromboembolism provoked by a transient risk factor.

D) Risk for Arterial Thrombosis

Arterial thrombosis is a common cause of hospital admission, death, and disability in developed countries (and increasingly in developing nations because of global epidemics of smoking, obesity, and diabetes). It usually follows spontaneous rupture of an atherosclerotic plaque, and may:

- Be clinically silent;
- Contribute to atherosclerotic progression resulting in coronary stenosis and stable angina, or lower limb artery stenosis and claudication:
- Be present as acute ischemia in the heart (acute coronary syndromes: unstable angina, myocardial infarction), brain (transient cerebral ischemic attack or stroke), or lim (acute limb ischemia).

Traditional risk factors (see table 2) remain the most important markers of arterial disease.

TABLE 2

| Risk factors |
|---|
| Dyslipemia |
| Current smoker |
| Diabetes |
| Hypertension |
| Abdominal obesity |
| Psychosocial factors |

The factor V Leiden and prothrombin G20210A mutations show modest but statistically significant associations with coronary heart disease, stroke, and peripheral arterial events, specially in younger persons (age under 55 years) and in women. The relationship of prothrombin G2010A with arterial thrombosis is very modest (OR 1.32; 95% CI 1.03-1.69) (Kim R J. Am Heart J 2003;146:948-957). The relationship of factor V Leiden mutation and arterial ischemic events is also modest (OR 1.21; 95% CI 0.99-1.49), patients <55 years old were at greater risk for arterial ischemic event (OR 1.37;95% CI 0.96-1.97) (Kim R J. Am Heart J 2003;146:948-957).

There is little evidence that other congenital thrombophilias are associated with increased risk of arterial disease.

Need for New Risk Factors

Despite the above mentioned existence of risk factors and diagnostic tools for early diagnosis arterial thrombosis and venous thromboembolism, which includes deep vein thrombosis and pulmonary embolism, are major causes of morbidity and mortality.

Even among high-risk groups it is not possible to identify individuals who will go on to develop thrombosis and/or venous thromboembolism. Therefore, although several strategies exist for both precise the identification of the risk to develop a thromboembolic event, its prevention or the precise diagnosis of a thromboembolic disease, the goal of preventing the clinical burden of thrombosis and/or thromboembolism has not yet been accomplished (Ruppert A. Current Medical Research & Opinion 2010;26:2465-2473).

Several attempts have been done to use molecular diagnostics to identify subjects at high risk to develop a trombotic and/or thromboembolic event. Starting from the finding of a common missense mutation in the factor V gene by Bertina (Bertina R M. Nature 1994;369:64-67), the description of the prothrombin 20210 3' non-coding sequence variant (Poort S R. Blood 1996;88:3698-3703), and the thermolabile C677T 5,10-methylene-tetrahydrofolate reductase variant. There is also patent document such as EP00696325B1 describing the use of mutations in coagulation factors. EP00696325B1 describes the use of mutations in factor V to identify persons at risk to develop thrombotic event. Or the patent document WO05047533A1 describing a method for detecting the presence or absence of a variant nucleotide in at least two SNP sites associated with thrombosis, said SNP sites selected from the group consisting of factor V Leiden G1691A, Prothrombin (Factor II) G20210A, MTHRF C677T, MTHFR A1298C, factor XIII G4377T, and tissue factor plasma inhibitors (TFPI) C536T.

However, none of the attempts tried until now have proved satisfactory efficacy and the initial enthusiasm for test adoption will need to be tempered by formal evidence of clinical benefit deriving from the test.

Accordingly, there is a need for novel markers, including new genetic markers and specific combinations thereof that would successfully and advantageously predict who is at high risk of developing a thromboembolic disease and/or thromboembolic disease complications such as—but not limited to—deep vein thrombosis, pulmonary embolism, acute coronary syndromes (acute myocardial infarction, unstable angina), stroke, transient ischemic attack or stroke in a way that preventive measures could be implemented to keep that risk at the lowest possible level.

There is also a need for novel markers, including new genetic markers and specific combinations thereof that would successfully and advantageously assist the diagnosis of a thromboembolic disease and/or thromboembolic disease complications such as—but not limited to—deep vein thrombosis, pulmonary embolism, acute coronary syndromes (acute myocardial infarction, unstable angina), stroke, transient ischemic attack or stroke in a way that preventive measures could be implemented to keep that risk at the lowest possible level.

SUMMARY OF THE INVENTION

In a first aspect, the invention provides a method which is suitable to solve the limitations of the methods used nowadays to estimate the thromboembolism risk and/or to diagnose the thromboembolic events for a particular subject.

The method provided according to the present invention solves the limitations comprising the steps of determining in a sample isolated from said subject the presence at least of one of following genetic variants Serpin A10 (protein Z inhibitor) Arg67Stop (rs2232698), Serpin C1 (antithrombin) Ala384Ser (Cambridge II), factor XII C46T (rs1801020), factor XIII Val134Leu (rs5985), Factor II (prothrombin) G20210A (rs1799963), factor V Leiden Arg506Gln (rs6025), factor V Cambridge Arg306Thr, factor V Hong Kong Arg306Gly, ABO blood group rs8176719, ABO blood group rs7853989, ABO blood group rs8176743, and ABO blood group rs8176750 is indicative of the risk of suffering a thromboembolic event (fatal or non-fatal acute myocardial infarction, or stroke, or transient ischemic attack, or peripheral arteriopathy or deep vein thrombosis or pulmonary embolism) which is better than the risk assessment done by the methods nowadays in use.

In another aspect, the invention relates to methods for the establishing the probability of an individual of presenting thromboembolic event based on the presence of one or more of the polymorphisms mentioned above in combination with one or more conventional risk factors, wherein the risk is given.

In another aspect, the invention relates to methods for the establishing the probability of an individual of presenting a recurrent thromboembolic event based on the presence of one or more of the polymorphisms mentioned above in combination with one or more conventional risk factors, sociodemographic and clinical characteristics, wherein the risk is given.

In another aspect, the invention relates to methods for the assistance to the diagnosis of a thromboembolic event based on the presence of one or more of the genetic variants mentioned above in combination with one or more conventional risk factors, sociodemographic and clinical characteristics, wherein the probability for diagnosis is given.

In another aspect, the invention relates to methods for the establishing the need for preventive measurements to prevent the development of a thromboembolic event based on the presence of one or more of the polymorphisms mentioned above in combination with one or more conventional risk factors, sociodemographic and clinical characteristics wherein the risk is given.

"Thromboembolic event" in the context of this application should be understood as the alteration of the hemostasis that leads to the development of a blood clot (thrombo) inside a vascular vessel (artery or vein). The thrombo can even obstruct the vascular vessel completely and/or become detached and obstruct another vascular vessel.

"Thromboembolic event" includes among others the following conditions: arterial thrombosis, fatal- and non-fatal myocardial infarction, stroke, transient ischemic attacks, cerebral venous thrombosis, peripheral arteriopathy, deep vein thrombosis and pulmonary embolism.

"Thromboembolic event" in the context of this application is used interchangeably with "thromboembolism".

"Thromboembolic event" in the context of this application is used interchangeably with "thrombosis".

"Thromboembolic event" in the context of this application is used interchangeably with "thromboembolic complication".

"Thrombophilia" in the context of this application should be understood as the disorders of hemostasis that predispose to thrombosis. Included are heritable deficiencies of the natural anticoagulants antithrombin, protein C, and protein S and common mutations in the genes encoding clotting factors and acquired thrombophilias such as antiphospholipid antibodies.

The terms "disease" and "disorder" shall be interpreted in the context of this application interchangeably.

"Mutation" in the context of this application should be understood as the change of the structure of a gene, resulting in a variant form which may be transmitted to subsequent generations, caused by the alteration of single base units in DNA, or the deletion, insertion, or rearrangement of larger sections of genes or chromosomes.

"Genetic variants" in the context of this application refers to genetic differences both within and among populations. There may be multiple variants of any given gene in the human population (alleles), leading to polymorphism.

The terms "polymorphism" and "single nucleotide polymorphism" (SNP) are used herein interchangeably and relate to a nucleotide sequence variation occurring when a single nucleotide in the genome or another shared sequence differs between members of species or between paired chromosomes in an individual. A SNP can also be designated as a mutation with low allele frequency greater than about 1% in a defined population. Single nucleotide polymorphisms according to the present application may fall within coding sequences of genes, non-coding regions of genes or the intronic regions between genes.

The term "sample", as used herein, refers to any sample from a biological source and includes, without limitation, cell cultures or extracts thereof, biopsied material obtained from a mammal or extracts thereof, and blood, saliva, urine, feces, semen, tears, or other body fluids or extracts thereof.

"Conventional risk factors" in the context of this application should be understood as those described in tables 1 and 2.

"Sociodemographic and clinical characteristics" in the context of this application should be understood as age, gender, diabetes mellitus, smoking, family history of thromboembolic event, pregnancy, and body mass index.

In a further aspect, the invention relates to a computer program or a computer-readable media containing means for carrying out any of the methods of the invention.

In yet a further aspect, the invention relates to a kit comprising reagents for detecting the genetic variants Serpin A10 (protein Z inhibitor) Arg67Stop (rs2232698), Serpin C1 (antithrombin) Ala384Ser (Cambridge II), factor XII C46T (rs1801020), factor XIII Val34Leu (rs5985), Factor II (prothrombin) G20210A (rs1799963), factor V Leiden Arg506Gln (rs6025), factor V Cambridge Arg306Thr, factor V Hong Kong Arg306Gly, ABO blood group rs8176719, ABO blood group rs7853989, ABO blood group rs8176743, and ABO blood group rs8176750.

BRIEF DESCRIPTION OF THE DRAWINGS

FIG. 1a shows a HairLoop™ in a closed state, in the absence of a DNA target. FIG. 1b shows that when the target binds perfectly (no mismatch) to its HairLoop™, the greater stability of the probe-target duplex forces the stem to unwind, resulting in an opening of the HairLoop™.

DETAILED DESCRIPTION OF THE INVENTION

Figure 1A:
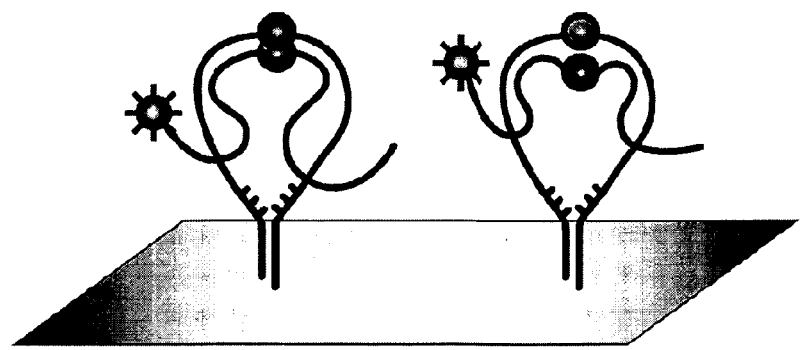
FIGS. 1a and 1b depict an example of a HairLoop™ with its hairpin stem, which is attached to the microarray surface by only one of its strands.

The authors of the present invention have solved the problems identified above in the methods in use nowadays for the calculation of the risk in a subject to develop a thromboembolic event, as this term has been defined above.

The authors of the present invention have identified a series of genetic variants which are associated with a risk of presenting a thromboembolic event. These genetic variants show predictive and diagnostic value.

Method for Solving the Limitations of the Methods to the Prediction of the Risk to Develop a Thromboembolic Event or for the Diagnosis of a Thromboembolic Event.

The present application solves the above-described limitation of the methods used nowadays to calculate the thromboembolic event risk and/or to diagnosis a thromboembolic event. A particular combination (as described above) of genetic markers is used, selected and evaluated by the inventors after a complex and genuine analysis of thousands of possible markers. Of the different possibilities to construct a genetic risk score (GRS), the inventors have selected a particular one because it provided the best possible results. To calculate the genetic risk punctuation, the accumulated number of risk allele risk from those SNPs listed in table 3 that are present in each individual is considered. For each of the variants studied, every individual can have 0, 1 or 2 alleles of risk. On having calculated the summatory of risk alleles accumulated in the different set of the selected variants (n=12), for each individual a score that could go from 0 to 24 was given. The inventors have generated new algorithms for thromboembolic risk estimation.

TABLE 3

| Gene | SNP (draft name) | Reference ID of the variant | rs | Informative allele | Other allele |
|---|---|---|---|---|---|
| FXII | 46C > T | FXII, 46C > T | 1801020 | T | C |
| ABO blood group (A1 allele) | 261delG | ABO blood group | 8176719 | G | delG |
| | 526C > G | ABO blood group | 7853989 | C | G |
| | 703G > A | ABO blood group | 8176743 | G | A |
| | 1059 delC | ABO blood group | 8176750 | C | delC |
| SERPIN A10 | 728C > T | Serpin A10, Arg67Stop | 2232698 | T | C |
| SERPINC1 | SerpinC1, Ala384Ser (Cambridge II) | SerpinC1, Ala384Ser (Cambridge II) | — | T | G |
| coagulation factor FV | FV Leiden (1746G > A) | FV, R506Q (F5 Leiden) | 6025 | A | G |
| | FV Cambridge (1146G > C) | FV, R306T (F5 Cambridge) | — | C | G |
| | FV Hong Kong (1145A > G) | FV, R306G (F5 Hong Kong) | — | G | A |
| coagulation factor XIII (A1 polypeptide) | V34L (226G > T) | FXIII, Val34Leu, rs | 5985 | G | T |
| coagulation factor II | G20210A | Prothrombin, G20210A | 1799963 | A | G |

The list of polymorphisms which are used in this method of the present invention is given in Table 3.

When prediction models are used, as for instance, for making treatment decisions, predictive risks may be categorized by using risk cutoff thresholds.

Those skilled in the art will readily recognize that the analysis of the nucleotides present according to the method of the invention in an individual's nucleic acid can be done by any method or technique capable of determining nucleotides present in a polymorphic site. As it is obvious in the art, the nucleotides present in the polymorphic markers can be determined from either nucleic acid strand or from both strands.

Once a biological sample from a subject has been obtained (e.g., a bodily fluid, such as urine, saliva, plasma, serum, or a tissue sample, such as a buccal tissue sample or a buccal cell) detection of a sequence variation or allelic variant SNP is typically undertaken. Virtually any method known to the skilled artisan can be employed. Perhaps the most direct method is to actually determine the sequence of either genomic DNA or cDNA and compare these sequences to the known alleles SNPs of the gene. This can be a fairly expensive and time-consuming process. Nevertheless, this technology is quite common and is well known.

Any of a variety of methods that exist for detecting sequence variations may be used in the methods of the invention. The particular method used is not important in the estimation of cardiovascular risk or treatment selection.

Other possible commercially available methods exist for the high throughput SNP identification not using direct sequencing technologies, for example, Illumina's Veracode Technology, Taqman® SNP Genotyping Chemistry and KASPar SNP genotyping Chemistry.

A variation on the direct sequence determination method is the Gene Chip™ method available from Affymetrix. Alternatively, robust and less expensive ways of detecting DNA sequence variation are also commercially available. For example, Perkin Elmer adapted its TAQman Assay™ to detect sequence variation. Orchid BioSciences has a method called SNP-IT™ (SNP-Identification Technology) that uses primer extension with labeled nucleotide analogs to determine which nucleotide occurs at the position immediately 3' of an oligonucleotide probe, the extended base is then identified using direct fluorescence, an indirect colorimetric assay, mass spectrometry, or fluorescence polarization. Sequenom uses a hybridization capture technology plus MALDI-TOF (Matrix Assisted Laser Desorption/Ionization-Time-of-Flight mass spectrometry) to detect SNP genotypes with their MassARRAY™ system. Promega provides the READIT™ SNP/Genotyping System (U.S. Pat. No. 6,159,693). In this method, DNA or RNA probes are hybridized to target nucleic acid sequences. Probes that are complementary to the target sequence at each base are depolymerized with a proprietary mixture of enzymes, while probes which differ from the target at the interrogation position remain intact. The method uses pyrophosphorylation chemistry in combination with luciferase detection to provide a highly sensitive and adaptable SNP scoring system. Third Wave Technologies has the Invader OS™ method that uses proprietary Cleaveseg enzymes, which recognize and cut only the specific structure formed during the Invader process. Invader OS relies on linear amplification of the signal generated by the Invader process, rather than on exponential amplification of the target. The Invader OS assay does not utilize PCR in any part of the assay. In addition, there are a number of forensic DNA testing labs and many research labs that use gene-specific PCR, followed by restriction endonuclease digestion and gel electrophoresis (or other size separation technology) to detect restriction fragment length polymorphisms (RFLPs).

In various embodiments of any of the above aspects, the presence or absence of the SNPs is identified by amplifying or failing to amplify an amplification product from the sample. Polynucleotide amplifications are typically template-dependent. Such amplifications generally rely on the existence of a template strand to make additional copies of the template. Primers are short nucleic acids that are capable of priming the synthesis of a nascent nucleic acid in a template-dependent process, which hybridize to the template strand. Typically, primers are from ten to thirty base pairs in length, but longer sequences can be employed. Primers may be provided in double-stranded and/or single-stranded form, although the single-stranded form generally is preferred. Often, pairs of primers are designed to selectively hybridize to distinct regions of a template nucleic acid, and are contacted with the template DNA under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

Polymerase Chain Reaction

A number of template dependent processes are available to amplify the oligonucleotide sequences present in a given template sample. One of the best known amplification methods is the polymerase chain reaction. In PCR, pairs of primers that selectively hybridize to nucleic acids are used under conditions that permit selective hybridization. The term "primer", as used herein, encompasses any nucleic acid that is capable of priming the synthesis of a nascent nucleic acid in a template-dependent process. Primers may be provided in double-stranded or single-stranded form, although the single-stranded form is preferred. Primers are used in any one of a number of template dependent processes to amplify the target gene sequences present in a given template sample. One of the best known amplification methods is PCR, which is described in detail in U.S. Pat. Nos. 4,683,195, 4,683,202 and 4,800,159, each incorporated herein by reference. In PCR, two primer sequences are prepared which are complementary to regions on opposite complementary strands of the target-gene(s) sequence. The primers will hybridize to form a nucleic-acid:primer complex if the target-gene(s) sequence is present in a sample. An excess of deoxyribonucleoside triphosphates is added to a reaction mixture along with a DNA polymerase, e.g. Taq polymerase that facilitates template-dependent nucleic acid synthesis. If the target-gene(s) sequence:primer complex has been formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles", are conducted until a sufficient amount of amplification product is produced.

The amplification product may be digested with a restriction enzyme before analysis. In still other embodiments of any of the above aspects, the presence or absence of the SNP is identified by hybridizing the nucleic acid sample with a primer labeled with a detectable moiety. In other embodiments of any of the above aspects, the detectable moiety is detected in an enzymatic assay, radioassay, immunoassay, or by detecting fluorescence. In other embodiments of any of the above aspects, the primer is labeled with a detectable dye (e.g., SYBR Green I, YO-PRO-I, thiazole orange, Hex, pico green, edans, fluorescein, FAM, or TET). In other embodiments of any of the above aspects, the primers are located on a chip. In other embodiments of any of the above aspects, the primers for amplification are specific for said SNPs.

Another method for amplification is the ligase chain reaction ("LCR"). LCR differs from PCR because it amplifies the probe molecule rather than producing an amplicon through polymerization of nucleotides. In LCR, two complementary probe pairs are prepared, and in the presence of a target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

Isothermal Amplification

An isothermal amplification method, in which restriction endonucleases and ligases are used to achieve the amplification of target molecules that contain nucleotide 5'-[[alpha]-thio]-triphosphates in one strand of a restriction site also may be useful in the amplification of nucleic acids in the present invention. In one embodiment, loop-mediated isothermal amplification (LAMP) method is used for single nucleotide polymorphism (SNP) typing.

Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection.

Transcription-Based Amplification

Other nucleic acid amplification procedures include transcription-based amplification systems, including nucleic acid sequence based amplification. In nucleic acid sequence based amplification, the nucleic acids are prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer, which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Other amplification methods may be used in accordance with the present invention. In one embodiment, "modified" primers are used in a PCR-like, template and enzyme dependent synthesis. The primers may be modified by labelling with a capture moiety (e.g., biotin) and/or a detector moiety (e.g., enzyme). In the presence of a target sequence, the probe binds and is cleaved catalytically. After cleavage, the target sequence is released intact to be bound by excess probe. Cleavage of the labelled probe signals the presence of the target sequence. In another approach, a nucleic acid amplification process involves cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Methods for Nucleic Acid Separation

It may be desirable to separate nucleic acid products from other materials, such as template and excess primer. In one embodiment, amplification products are separated by agarose, agarose-acrylamide or polyacrylamide gel electrophoresis using standard methods (Sambrook et al., 1989, see infra). Separated amplification products may be cut out and eluted from the gel for further manipulation. Using low melting point agarose gels, the separated band may be removed by heating the gel, followed by extraction of the nucleic acid. Separation of nucleic acids may also be effected by chromatographic techniques known in the art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC. In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to X-ray film or visualized with light exhibiting the appropriate excitatory spectra.

Alternatively, the presence of the polymorphic positions according to the methods of the invention can be determined by hybridisation or lack of hybridisation with a suitable nucleic acid probe specific for a polymorphic nucleic acid but not with the non-mutated nucleic acid. By "hybridize" is meant a pair to form a double-stranded molecule between complementary polynucleotide sequences, or portions thereof, under various conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 [mu]g/ml denatured salmon sperm DNA (ssDNA). In a most preferred embodiment, hybridization will occur at 42° C. in 250 mM NaCl, 25 mM trisodium citrate, 1% SDS, 50% formamide, and 200 [mu]g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York, 1989.

Nucleic acid molecules useful for hybridisation in the methods of the invention include any nucleic acid molecule which exhibits substantial identity so as to be able to specifically hybridise with the target nucleic acids. Polynucleotides having "substantial identity" to an endogenous sequence are typically capable of hybridizing with at least one strand of a double-stranded nucleic acid molecule. By "substantially identical" is meant a polypeptide or nucleic acid molecule exhibiting at least 50% identity to a reference amino acid sequence or nucleic acid sequence. Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

A detection system may be used to measure the absence, presence, and amount of hybridization for all of the distinct sequences simultaneously. Preferably, a scanner is used to determine the levels and patterns of fluorescence.

Another method for detecting sequence variations is based on the amplification by PCR of specific human targets and the subsequent detection of their genotype by hybridization to specific Hairloop™ probes spotted on a microarray.

Figure 1B:
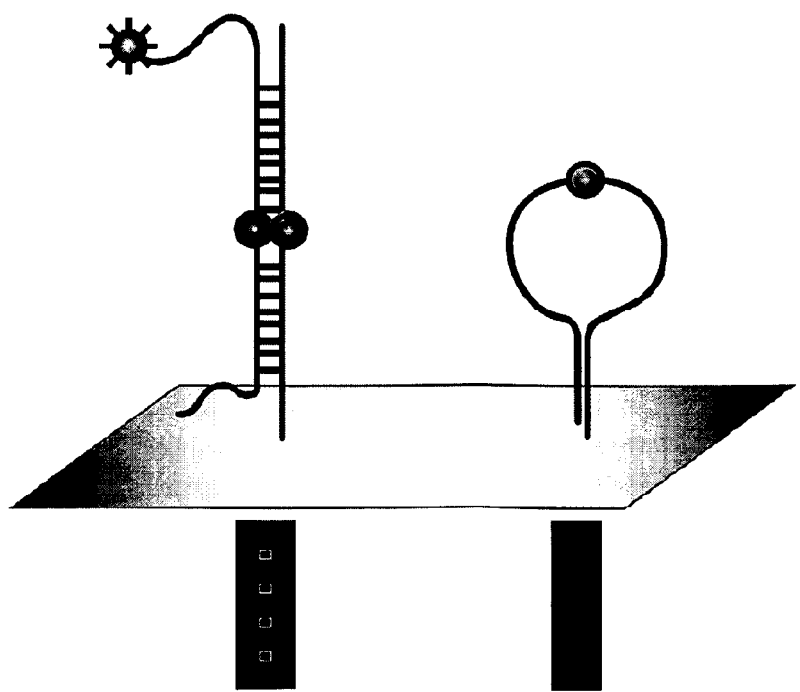

HairLoop™ is a stem-loop, single-stranded DNA molecule consisting of a probe sequence embedded between complementary sequences that form a hairpin stem. The stem is attached to the microarray surface by only one of its strands. In the absence of a DNA target, the HairLoop™ is held in the closed state (FIG. 1a). When the target binds perfectly (no mismatch) to its HairLoop™, the greater stability of the probe-target duplex forces the stem to unwind, resulting in an opening of the HairLoop™ (FIG. 1b). Due to these unique structural and thermodynamic properties, HairLoop™ offer several advantages over linear probes, one of which is their increased specificity differentiating between two DNA target sequences that differ by as little as a single nucleotide.

HairLoop™ act like switches that are normally closed, or "off". Binding to fluorescent DNA target induces conformational changes that open the structure and as a result after washing, the fluorescence is visible, or "on".

One HairLoop™ is designed to be specific to one given allele. Thus, assessment of a point mutation for a bi-allelic marker requires two HairLoop™; one for the wild-type allele, and one for the mutant allele. The specific sequences for the detection of the polymorphisms described in table 3 using the HarLoop technology are given in table 4.

TABLE 4

| SEQ ID NO: | Variant name | Sequence comprising the polymorphism | Allele | dbSNP accession number | Chrom. | Position in chrom. | Strand |
|---|---|---|---|---|---|---|---|
| 1 | FXII, 46 C > T | GGACGGATGCCATGA | Risk | rs1801020 | 5 | 176836532 | + |
| 2 | | GGACGGACGCCATGA | Non-risk | | | | |
| 3 | ABO, 261deIG | CTCGTGGTGACCCCT | Risk | rs8176719 | 9 | 136132908 | - |
| 4 | | CTCGTGGT ACCCCTT | Non-risk | | | | |
| 5 | ABO, 526C > G | GGAGGTGCGCGCCT | Risk | rs7853989 | 9 | 136131592 | + |
| 6 | | GGAGGTGGGCGCCT | Non-risk | | | | |
| 7 | ABO, 703G > A | TGCACCCCGGCTTCTAC | Risk | rs8176743 | 9 | 136131415 | + |
| 8 | | TGCACCCCAGCTTCTAC | Non-risk | | | | |
| 9 | ABO, 1059deIC | TCCGGAACCCGTGAGC | Risk | rs8176750 | 9 | 136131059 | + |
| 10 | | TCCGGAA CCGTGAGCG | Non-risk | | | | |
| 11 | SERPINA10, 728 C > T | CCTGCTGTGAAAGATCT | Risk | rs2232698 | 14 | 94756669 | + |
| 12 | | CCTGCTGCGAAAGATCT | Non-risk | | | | |
| 13 | SERPINC1, Ala384Ser (Cambridge II) | CGGTACTTGAAGCTGCTT | Risk | NA | 1 | 173873176 | - |
| 14 | | CGGTACTTGCAGCTGCTT | Non-risk | | | | |
| 15 | FV, R506Q (FV Leiden) | ATTCCTTGCCTGTCC | Risk | RS6025 | 1 | 169519049 | - |
| 16 | | ATTCCTCGCCTGTCC | Non-risk | | | | |
| 17 | FV, R306T (FV Cambrigde) | GAAAACCACGAATCTTAAG | Risk | NA | 1 | 169524537 | + |
| 18 | | GAAAACCAGGAATCTTAAG | Non-risk | | | | |
| 19 | FV, R306G (FV Hong Kong) | AAGAAAACCGGGAATCTTA | Risk | NA | 1 | 169524536 | + |
| 20 | | AAGAAAACCAGGAATCTTA | Non-risk | | | | |
| 21 | FXIII, Val34Leu | GGGCACCACGCCCTGA | Risk | rs5985 | 6 | 6318795 | - |
| 22 | | GGGCACCAAGCCCTGA | Non-risk | | | | |
| 23 | Prothrombin, G20210A | TCTCAGCAAGCCTCAAT | Risk | rs1799963 | 11 | 46761055 | + |
| 24 | | TCTCAGCGAGCCTCAAT | Non-risk | | | | |

Method to Establish in a More Appropriate Way the Risk Status.

Another object of the present invention is the development of an algorithm to estimate the risk to develop and/or to being suffering a thromboembolic event. The algorithm is shown as functions 1.

Function 1

Estimating the risk of thrombosis.

The individual estimation of the risk of thrombosis is based on a logistic regression model. The aim of this model is to calculate the probability that a person has of presenting venous thrombosis according to his/her genetic, sociodemographic and clinical characteristics. To calculate this probability we use the following equation:

$$\text{Probability}(Y=1|x_1,\ldots,x_n) = 1/1+\exp(\beta_0 + \beta_1 x_1 + \ldots + \beta_n x_n + \beta_{fg} x_f x_g + \ldots + \beta_{h \cdot i} x_h \cdot x_i),$$

wherein:

Probability($Y=1|x_1, \ldots, x_n$)=probability of presenting a thrombosis in a particular individual with concrete and measurable characteristics in a number of variables 1, . . . , n. This probability could range between 0 and 1;

Exp=exponential natural base;

$\beta_0$=coefficient that defines the risk (the probability) of thrombosis non related with the variables 1 to n. This coefficient can take a value from $-\infty$ to $+\infty$ and is calculated as the natural logarithm of the incidence of venous thrombosis in the population;

$\beta_1$=regression coefficient that expresses the risk (higher or lower) to present thrombosis associated with the value/presence of the predictor variable $x_1$. This coefficient can take a value from $-\infty$ to $+\infty$;

$x_1$=value taken by the predictor variable $x_1$ in an individual. The range of possible values depends on the variable;

$\beta_n$=regression coefficient that expresses the risk (higher or lower) to present thrombosis associated with the value/presence of the predictor variable $x_n$. This coefficient can take a value from $-\infty$ to $+\infty$;

$x_n$=value taken by the predictor variable $x_n$ in an individual. The range of possible values depends on the variable.

In addition, the model includes the effect of the combination of some variables in terms of interaction or modification of the effect. That is, the effect size (regression coefficient) of a single variable ($x_f$) can be $\beta_f$ but if this variable is present in combination with another variable ($x_g$) the effect size may vary (increase or decrease) and therefore to consider the effect size of the variable $x_f$ we will have to consider not only the $\beta_f$ but also a second regression coefficient $\beta_{fg}$ by adding the $\beta_f$ and the $\beta_{fg}$. Thus:

$\beta_{fg}$=regression coefficient that expresses the risk (higher or lower) to present thrombosis associated with the combined presence of the predictor variables $x_f$ and $x_g$. This coefficient can take a value from $-\infty$ to $+\infty$;

$x_f$=value taken by the predictor variable $x_f$ in an individual. The range of possible values depends on the variable;

$x_g$=value taken by the predictor variable $x_f$ in an individual. The range of possible values depends on the variable;

$\beta_{h,i}$=regression coefficient that expresses the risk (higher or lower) to present thrombosis associated with the combined presence of the predictor variables $x_h$ and $x_i$. This coefficient can take a value from $-\infty$ to $+\infty$;

$x_h$=value taken by the predictor variable $x_h$ in an individual. The range of possible values depends on the variable;

$x_i$=value taken by the predictor variable $x_i$ in an individual. The range of possible values depends on the variable;

If the patient does not present any mutation or genetic variant of risk but he/she presents a positive family history of venous thrombosis we will include this variable in the model. The regression coefficient of this variable is 1,185 with a range of possible values from 0.200 to 2.500.

The variables included in the model and the regression coefficients of each of these variables are shown in table 5.

TABLE 6

Definition of A1 allele
The subject carries at least one A1 allele at ABO locus is any of the following combinations is present:

| | Genotypes | | | |
|---|---|---|---|---|
| Combination | rs8176719 | rs7853989 | rs8176743 | rs8176750 |
| 1 | GG | CC | GG | CC |
| 2 | GG | CC | GG | CdelC |
| 3 | GG | CG | GA | CG |
| 4 | GdelG | CC | GG | CG |
| 5 | GG | CG | GG | CC |

Surprisingly, the combination of SNP markers included in the present invention and set forth in table 3 and using the function described in function 1 have proved to be capable to establishing the risk to develop a thromboembolic disease or event with a higher accuracy than that obtained using the methods nowadays in use or published functions including genetic information.

Surprisingly, the combination of SNP markers included in the present invention and set forth in table 3 and using the

TABLE 5

| Variable | | Risk exposure | Regression coefficient | Regression coefficient lower limit | Regression coefficient upper limit |
|---|---|---|---|---|---|
| Clinical | | | | | |
| Age | <55 y | No | 0 | | |
| | 55-64 | Yes | 0.811 | 0.100 | 3.000 |
| | 65-74 | Yes | 1.409 | 0.100 | 3.000 |
| | 75-84 | Yes | 1.681 | 0.100 | 3.000 |
| | >84 | Yes | 2.534 | 0.500 | 6.000 |
| Male | | Yes | 0.336 | 0.050 | 1.500 |
| Diabetes | | Yes | 0.351 | 0.050 | 1.500 |
| Smoking | | Yes | 0.166 | 0.050 | 1.500 |
| Body mass index | <25 kg/m$^2$ | No | 0 | 0 | 0 |
| | 25-29.9 kg/m$^2$ | Yes | 0.412 | 0.050 | 1.500 |
| | ≥30 kg/m$^2$ | Yes | 0.820 | 0.100 | 3.000 |
| Use of oral contraceptives | | Yes | 1.131 | 0.100 | 3.000 |
| Pregnancy | | Yes | 1.435 | 0.100 | 3.000 |
| Family history of thrombosis* | | Yes | 1.185 | 0.100 | 3.000 |
| Genetic | | | | | |
| Factor V Leiden Heterozygote | | AG | 0.993 | 0.100 | 3.000 |
| Factor V Leiden Homozygote | | AA | 2.890 | 0.500 | 6.000 |
| Protombin | | AG | 0.293 | 0.050 | 1.500 |
| Serpin10 | | TG | 1.358 | 0.100 | 3.000 |
| Factor XII | | TC/TT | 1.633 | 0.100 | 3.000 |
| Factor XIII | | GT/GG | 0.198 | 0.050 | 1.500 |
| SerpinC | | TG | 2.277 | 0.500 | 6.000 |
| ABO (A1 allele) | | (see table 6) | 0.956 | 0.100 | 3.000 |
| Interactions | | | | | |
| Factor V Leiden · Protombin | | AG · AG | 1.114 | 0.100 | 3.000 |
| Factor V Leiden · ABO | | AG · (see table 6) | 0.599 | 0.100 | 3.000 |
| Factor V Leiden · Oral contraceptives | | AG · Yes | 0.028 | 0.005 | 1.000 |
| Factor V Leiden · Pregnancy | | AG · Yes | 1.191 | 0.100 | 3.000 |
| Protrombin · Oral contraceptives | | AG · Yes | 0.542 | 0.100 | 3.000 |
| Protrombin · Pregnancy | | AG · Yes | 1.673 | 0.100 | 3.000 |
| Protrombin · BMI ≥30 kg/m$^2$ | | AG · Yes | 0.772 | 0.100 | 3.000 |
| Oral contraceptives · BMI ≥30 kg/m$^2$ | | Yes · Yes | 1.218 | 0.100 | 3.000 |

*Only included in the model if the patient does not present any mutation or genetic variant of risk but he/she presents a positive family history of venous thrombosis.

function described in function 1 have proved to be capable to assist in the diagnosis of a thromboembolic disease or event with a higher accuracy than that obtained using the methods nowadays in use or published functions including genetic information.

By the use of the functions described, a personalized risk is obtained for the development of thromboembolic event, in particular fatal- and non-fatal-myocardium infarction, stroke, transient ischemic attack, peripheral arteriopathy, deep vein thrombosis, pulmonary embolism or a combination thereof.

EXAMPLE 1 introduction. Thromboembolic disease has an important genetic component. In addition to the classic FV Leiden (FVL) and prothrombin G20210A (PT), new genetic variants associated with this pathology have been identified. The aim of this study was to determine whether a set of genetic variants selected by us (genetic profile) improves the ability of FVL and PT to predict the presence of thrombosis.

Methods. We included two studies (thrombosis) and controls: MARTHA (1,150 casos/801 controls) designed to evaluate the association of FVL and PT with other risk factors, and a study in Spanish population: PE (249 casos/ 248 controls). The genetic profile analyzed was: FVL, PT, ABO, C46T (F12), A384S (SERPINC1), R67X (SER-PINA10). The association between genetic variants and thrombosis was calculated using the OR adjusted for age and sex. The predictive ability was calculated using the c statistic (AUC-ROC) and reclassification (NRI, IDI) observed when using the FVL, PT or when using the genetic profile.

Results.

TABLE 7

Association between variants and thrombosis [OR (95%)] and the proportion of FVL and PT carriers compared with carriers of the genetic profile (only cases).

|  | FVL | PT | A1 | C46T | A384S | R67X |
| --- | --- | --- | --- | --- | --- | --- |
| MARTHA | 2.3 (1.8-2.8) | 0.9 (0.7-1.1) | 1.8 (1.2-2.7) | 0.9 (0.6-1.4) | 0.9 (0.2-3.7) | 2.3 (1.2-4.6) |
| Cases | 50.4 | | | | | |
| | | | 87.5 | | | |
| PE | 7.2 (2.8-18.9) | 2.8 (1.2-6.8) | 2.62 (1.8-3.8) | 3.1 (1.1-8.8) | 4.1 (0.5-36.9) | 2.5 (0.8-8.1) |
| Cases | 19.7 | | | | | |
| | | | 71.5 | | | |

TABLE 8

Estadigraf c and reclassification, NRI (net reclassification improvement) and IDI (integrated discrimination improvement) comparing the use of the genetic profile to FVL and PT.

| | Estadiraf c | | NRI | | IDI | |
| --- | --- | --- | --- | --- | --- | --- |
| | MARTHA | PE | MARTHA | PE | MARTHA | PE |
| FVL + PT | 0.54 (0.51-0.57) | 0.58 (0.56-0.62) | Ref. | Ref. | Ref | Ref. |
| FVL + PT + Resto | 0.58 (0.55-0.61) | 0.69 (0.64-0.73) | 5.3 (−1.1-11.6); | 23.4 (11.1-35.6) | 1 (0.3-1.8) | 5.9 (3.71-7.88) |
| P-value | <0.001 | <0.001 | >0.05 | <0.001 | <0.05 | <0.001 |

Discussion. We demonstrate that the selected generic profile significantly improves the prediction of the risk of thrombosis, identifying a genetic risk of presenting a thromboembolic event in 51.6% of people who had a thromboembolic event and through analysis of FVL and PT were not at risk genetic. The genetic profile in clinical practice will improve the diagnosis, prevention and treatment of thromboembolic disease.

The invention claimed is:

1. A method comprising detecting the presence or absence of a combination of single nucleotide polymorphisms (SNPs) in a biological sample isolated from a human subject, wherein the combination of SNPs consists of: Serpin A10 (protein Z inhibitor) Arg67Stop (rs2232698), Serpin C1(antithrombin) Ala384Ser (Cambridge II), factor XII C46T (rs1801020), factor XIII Val34Leu (rs5985), Factor II (prothrombin) G20210A (rs1799963), factor V Leiden Arg506Gln (rs6025), factor V Cambridge Arg306Thr, factor V Hong Kong Arg306Gly, ABO blood group rs8176719, ABO blood group rs7853989, ABO blood group rs8176743, and ABO blood group rs8176750 wherein the presence or absence of the polymorphisms is identified by hybridization to specific probes consisting of SEQ ID NO:s: 1 to 24 spotted on a microarray.

2. The method as defined in claim 1, further comprising determining one or more characteristics of the subject selected from the group consisting of age, race, sex, body mass index, smoking status, systolic blood pressure, diastolic blood pressure, hospitalization, plaster cast immobilization, surgery, trauma, oral contraceptives or hormone therapy, pregnancy, prolonged travel, collagen vascular diseases, heart failure, malignancy, medications, myelo proliferative disorders, nephrotic syndrome, recurrent pregnancy loss, abdominal obesity, diabetes mellitus, low density lipoprotein (LDL)-cholesterol level, high density lipoprotein (HDL)-cholesterol level, cholesterol level, triglyceride levels, and family history of thromboembolic event.

3. The method of claim 2, wherein the prolonged travel is two hours or longer.

4. The method according to claim 1, wherein the biological sample is an oral tissue sample, scraping, or wash or a biological fluid sample.

5. The method of claim 4, wherein the biological fluid sample is saliva, urine, or blood.

* * * * *

SEQUENCE LISTING

<160> NUMBER OF SEQ ID NOS: 24

<210> SEQ ID NO 1
<211> LENGTH: 15
<212> TYPE: DNA
<213> ORGANISM: Artificial Sequence
<220> FEATURE:
<223> OTHER INFORMATION: oligonucleotide

<400> SEQUENCE: 1

```
ggacggatgc catga                                                    15

<210> SEQ ID NO 2
<211> LENGTH: 15
<212> TYPE: DNA
<213> ORGANISM: Artificial Sequence
<220> FEATURE:
<223> OTHER INFORMATION: oligonucleotide

<400> SEQUENCE: 2
ggacggacgc catga                                                    15

<210> SEQ ID NO 3
<211> LENGTH: 15
<212> TYPE: DNA
<213> ORGANISM: Artificial Sequence
<220> FEATURE:
<223> OTHER INFORMATION: oligonucleotide

<400> SEQUENCE: 3
ctcgtggtga cccct                                                    15

<210> SEQ ID NO 4
<211> LENGTH: 15
<212> TYPE: DNA
<213> ORGANISM: Artificial Sequence
<220> FEATURE:
<223> OTHER INFORMATION: oligonucleotide

<400> SEQUENCE: 4
ctcgtggtac ccctt                                                    15

<210> SEQ ID NO 5
<211> LENGTH: 14
<212> TYPE: DNA
<213> ORGANISM: Artificial Sequence
<220> FEATURE:
<223> OTHER INFORMATION: oligonucleotide

<400> SEQUENCE: 5
ggaggtgcgc gcct                                                     14

<210> SEQ ID NO 6
<211> LENGTH: 14
<212> TYPE: DNA
<213> ORGANISM: Artificial Sequence
<220> FEATURE:
<223> OTHER INFORMATION: oligonucleotide

<400> SEQUENCE: 6
ggaggtgggc gcct                                                     14

<210> SEQ ID NO 7
<211> LENGTH: 17
<212> TYPE: DNA
<213> ORGANISM: Artificial Sequence
<220> FEATURE:
<223> OTHER INFORMATION: oligonucleotide

<400> SEQUENCE: 7
tgcaccccgg cttctac                                                  17

<210> SEQ ID NO 8
<211> LENGTH: 17
<212> TYPE: DNA
```

```
<213> ORGANISM: Artificial Sequence
<220> FEATURE:
<223> OTHER INFORMATION: oligonucleotide

<400> SEQUENCE: 8
tgcaccccag cttctac                                                  17

<210> SEQ ID NO 9
<211> LENGTH: 16
<212> TYPE: DNA
<213> ORGANISM: Artificial Sequence
<220> FEATURE:
<223> OTHER INFORMATION: oligonucleotide

<400> SEQUENCE: 9
tccggaaccc gtgagc                                                   16

<210> SEQ ID NO 10
<211> LENGTH: 16
<212> TYPE: DNA
<213> ORGANISM: Artificial Sequence
<220> FEATURE:
<223> OTHER INFORMATION: oligonucleotide

<400> SEQUENCE: 10
tccggaaccg tgagcg                                                   16

<210> SEQ ID NO 11
<211> LENGTH: 17
<212> TYPE: DNA
<213> ORGANISM: Artificial Sequence
<220> FEATURE:
<223> OTHER INFORMATION: oligonucleotide

<400> SEQUENCE: 11
cctgctgtga aagatct                                                  17

<210> SEQ ID NO 12
<211> LENGTH: 17
<212> TYPE: DNA
<213> ORGANISM: Artificial Sequence
<220> FEATURE:
<223> OTHER INFORMATION: oligonucleotide

<400> SEQUENCE: 12
cctgctgcga aagatct                                                  17

<210> SEQ ID NO 13
<211> LENGTH: 18
<212> TYPE: DNA
<213> ORGANISM: Artificial Sequence
<220> FEATURE:
<223> OTHER INFORMATION: oligonucleotide

<400> SEQUENCE: 13
cggtacttga agctgctt                                                 18

<210> SEQ ID NO 14
<211> LENGTH: 18
<212> TYPE: DNA
<213> ORGANISM: Artificial Sequence
<220> FEATURE:
<223> OTHER INFORMATION: oligonucleotide

<400> SEQUENCE: 14
cggtacttgc agctgctt                                                 18
```

```
<210> SEQ ID NO 15
<211> LENGTH: 15
<212> TYPE: DNA
<213> ORGANISM: Artificial Sequence
<220> FEATURE:
<223> OTHER INFORMATION: oligonucleotide

<400> SEQUENCE: 15
attccttgcc tgtcc                                                        15

<210> SEQ ID NO 16
<211> LENGTH: 15
<212> TYPE: DNA
<213> ORGANISM: Artificial Sequence
<220> FEATURE:
<223> OTHER INFORMATION: oligonucleotide

<400> SEQUENCE: 16
attcctcgcc tgtcc                                                        15

<210> SEQ ID NO 17
<211> LENGTH: 19
<212> TYPE: DNA
<213> ORGANISM: Artificial Sequence
<220> FEATURE:
<223> OTHER INFORMATION: oligonucleotide

<400> SEQUENCE: 17
gaaaaccacg aatcttaag                                                    19

<210> SEQ ID NO 18
<211> LENGTH: 19
<212> TYPE: DNA
<213> ORGANISM: Artificial Sequence
<220> FEATURE:
<223> OTHER INFORMATION: oligonucleotide

<400> SEQUENCE: 18
gaaaaccagg aatcttaag                                                    19

<210> SEQ ID NO 19
<211> LENGTH: 19
<212> TYPE: DNA
<213> ORGANISM: Artificial Sequence
<220> FEATURE:
<223> OTHER INFORMATION: oligonucleotide

<400> SEQUENCE: 19
aagaaaaccg ggaatctta                                                    19

<210> SEQ ID NO 20
<211> LENGTH: 19
<212> TYPE: DNA
<213> ORGANISM: Artificial Sequence
<220> FEATURE:
<223> OTHER INFORMATION: oligonucleotide

<400> SEQUENCE: 20
aagaaaacca ggaatctta                                                    19

<210> SEQ ID NO 21
<211> LENGTH: 16
<212> TYPE: DNA
<213> ORGANISM: Artificial Sequence
<220> FEATURE:
```

```
<223> OTHER INFORMATION: oligonucleotide

<400> SEQUENCE: 21
gggcaccacg ccctga                                                          16

<210> SEQ ID NO 22
<211> LENGTH: 16
<212> TYPE: DNA
<213> ORGANISM: Artificial Sequence
<220> FEATURE:
<223> OTHER INFORMATION: oligonucleotide

<400> SEQUENCE: 22
gggcaccaag ccctga                                                          16

<210> SEQ ID NO 23
<211> LENGTH: 17
<212> TYPE: DNA
<213> ORGANISM: Artificial Sequence
<220> FEATURE:
<223> OTHER INFORMATION: oligonucleotide

<400> SEQUENCE: 23
tctcagcaag cctcaat                                                         17

<210> SEQ ID NO 24
<211> LENGTH: 17
<212> TYPE: DNA
<213> ORGANISM: Artificial Sequence
<220> FEATURE:
<223> OTHER INFORMATION: oligonucleotide

<400> SEQUENCE: 24
tctcagcgag cctcaat                                                         17
```